United States Patent [19]
Laurila et al.

[11] Patent Number: 6,130,931
[45] Date of Patent: Oct. 10, 2000

[54] X-RAY FLUORESCENCE ELEMENTAL ANALYZER

[75] Inventors: Melvin J. Laurila, Lake Zurich, Ill.; Claus C Bachmann, Bad Wilbad; Albert P. Klein, Simmersfeld, both of Germany

[73] Assignee: Process Control, Inc., Wilmington, Del.

[21] Appl. No.: 09/156,078

[22] Filed: Sep. 17, 1998

[51] Int. Cl.$^7$ ................................................. G01N 23/223
[52] U.S. Cl. ................................ 378/45; 378/44; 378/54; 378/55
[58] Field of Search ................................ 378/44, 45, 54, 378/55

[56] References Cited

U.S. PATENT DOCUMENTS

| | | | |
|---|---|---|---|
| 3,864,570 | 2/1975 | Zingaro | 250/272 |
| 4,015,124 | 3/1977 | Page . | |
| 4,090,074 | 5/1978 | Watt et al. . | |
| 4,486,894 | 12/1984 | Page et al. . | |
| 4,550,768 | 11/1985 | McMullen et al. | 164/456 |
| 4,566,114 | 1/1986 | Watt . | |
| 4,582,992 | 4/1986 | Atwell et al. . | |
| 4,882,927 | 11/1989 | Gould | 73/1 R |
| 5,048,761 | 9/1991 | Kim | 241/19 |
| 5,261,977 | 11/1993 | Powell | 156/74 |
| 5,646,354 | 7/1997 | Lovejoy | 73/861.95 |
| 5,750,883 | 5/1998 | Elder | 73/53.01 |

OTHER PUBLICATIONS

Huber et al., "High performance, thermoelectrically cooled x-ray and gamma ray detectors", Nuclear Instruments and Methods in Physics Research B99, 665 (1995).

Ken Carr–Brion. X–Ray Analysers in Process Control (London: Elsevier 1989).

*Primary Examiner*—David V. Bruce
*Assistant Examiner*—Allen C Ho
*Attorney, Agent, or Firm*—King and Schickli, PLLC

[57] ABSTRACT

An apparatus for measuring the composition of coal and mineral ores on-line, by bombarding a sample stream with low energy X-rays and measuring the characteristic X-rays fluoresced. The assembly is comprised of one or more X-ray generators mounted in a specific geometry with one or more silicon detectors. A representative sample of a flow stream is obtained from a sampling system. Sample presentation to the analyzer is done with a plow or a flow cell to obtain a uniform interrogation zone for the analyzer. Elemental analysis (Aluminum through Silver on the Periodic Table) of the sample is computed from calibration curves generated from a linear relationship with count rates under each peak. Sample presentation to the analyzer is done with a plow or leveling plate to ensure that material flows past the analyzer at a constant level. The elemental analysis is determined by measuring counts under the characteristic peaks fluoresced by various elements in an energy spectrum resolved with a multi-channel analyzer.

22 Claims, 5 Drawing Sheets

X-RAY FLUORESCENCE ELEMENTAL ANALYZER

BACKGOUND AND SUMMARY OF THE INVENTION

This invention relates to a method and apparatus for analyzing the composition of coal, mineral ores and other products using energy dispersive X-ray fluorescence (XRF) spectroscopy. In the preparation and utilization of coal as a fuel, it is necessary to quantify the chemical and physical characteristics of the coal or ore. Coal purchases or trades are based on one or more of the following physical or chemical characteristics which are measured during the preparation and prior to the use of the coal feedstock:

Ash content
Moisture content
Calorific value content
Sulfur content
Elemental analysis In order to determine these characteristics the coal must be sampled, the sample prepared and then analyzed by standard laboratory procedures as set forth by organizations such as the American Society for Testing and Materials (ASTM) and/or the International Organization of Standardization (ISO). This is a costly and time consuming process requiring anywhere from two hours to more than a day to complete.

To address this problem, a number of coal analyzers have been developed. Most of these are ash analyzers and determine the ash content using dual energy transmission or backscatter of X- or γ-rays generated from two or more radioisotopes. A typical prior art system employs a low energy (<60 KeV) and a high energy (>600 KeV) γ-ray source to measure two signals which can be correlated to ash and density respectively. Watt (U.S. Pat. Nos. 4,090,074 and 4,566,114) uses any number of radioisotope sources from a group consisting of Am-241, Gd-153, Cd-109, Ba-133, Cs-137 and Co-57 to generate a series of incident X-and/or γ-ray energies that are transmitted or scattered through a layer of coal. The determination of the ash or mineral matter content in coal uses a transmission or scatter of X- or γ-rays at an energy where there is a significant difference in the absorption of radiation per unit weight in coal and mineral matter excluding iron (low energy ash measurement), in combination with a measurement of the bulk density (high energy). This is predominately the type of ash analyzer in use.

A variation of this ash analyzer was developed by Page as described in U.S. Pat. No. 4,486,894. An iron correction factor was incorporated into the ash determination. Low energy (<60 KeV) radiation bombards a sample with the primary radiation comprising at least two spectrums of energies (46 KeV and 9–17 KeV) to cause radiative reactions in the coal and measuring backscattered radiation in the same energy regions along with a fluoresced iron peak at 6.4 KeV. The fluoresced iron peak can also be related to the sulfur content in certain coals. Page (U.S. Pat. No. 4,015,124) approximated the sulfur content of a given type of coal using the multiple linear regression:

$$S = a + bX + cY$$

Where,
S=concentration of sulfur in the coal sample;
X=intensity of fluorescent radiation emitted by the sulfur in the sample;
Y=intensity of fluorescent radiation emitted by the iron in the sample; and
a,b, and c are constants.

However, the sulfur peak (X) could not be accurately measured and the relationship breaks down when iron pyrites ($FeS_2$) are either not found in sufficient concentrations to detect with a proportional counter or cannot be directly related to the total sulfur content.

Prior art use of X-ray fluorescence for elemental analysis, and particularly, sulfur, has been limited by the fact that the characteristic sulfur Kα X-ray emitted has an energy of only 2.31 KeV. Thus, the X-ray is quickly dissipated in coal (within 1 mm) or even air. To complicate the measurement, sulfur typically occurs in concentrations of less than 0.3% in coal. Marshall, in U.S. Pat. No. 4,171,485 states that the use of X-ray fluorescence other than for gaseous materials requires either the preparation or vaporization of a sample in an atmosphere which does not confuse the measurement. In either case, a difficult sampling and sample-preparation problem compounds the errors associated with X-ray fluorescence itself The better method in current use for determining sulfur content as well as several other elements present in the coal is to directly measure the different secondary, characteristic γ-ray energies emitted by the different elements when coal or mineral ores are bombarded by neutrons. This measurement process, as described by Marshall (see reference above) and Atwell in U.S. Pat. No. 4,582,992 is known in the art as prompt gamma ray neutron activation analysis (PGNAA). This technique is based on the fact that almost all elements when bombarded by slow neutrons capture these neutrons at least momentarily and form a compound nucleus in an excited state. Usually the prompt emission of one or more γ-rays with energies and intensities that are uniquely characteristic of the captured nucleus dissipates most of the excitation energy. Because these prompt γ-rays often have energies in the 2 to 11 MeV range, they can penetrate substantial quantities of material to reach a γ-ray detector, i.e., NaI(Ti) scintillation detector.

However, because of the high energies necessary to obtain sufficient penetration of flowing coal streams containing particles with top sizes of 2–4 inches, this technique is costly since neutron emitters and the necessary shielding is involved. X-ray fluorescence provides a safer and less expensive alternative if the sample presentation and X-ray detection problems can be solved.

The present invention addresses both sampling and X-ray detection in the design of a system that will mount directly on a sampling system using a thermoelectrically cooled Si-PIN photodiode X-ray detector.

Detectors used in X-ray spectroscopy in prior art systems for measuring the composition of coal and mineral ores, have been gas filled proportional counters, typically using a low density fill gas such as Neon or Xenon mixed with Argon. The resolution of 600 eV (FWHM) for proportional counters at low X-ray energies (less than Fe at 6.4 KeV) does not enable accurate determination of elements such as sulfur, silica or aluminum. By contrast, a Si-PIN detector has a resolution of 186 eV (FWHM) for a $^{55}$Fe X-ray at 5.9 KeV. Other silicon or semiconductor detectors e.g., Si(Li) can achieve similar high resolutions, but require enclosure in a vacuum cryostat and liquid nitrogen cooling. This seriously limits the applications in which the system can be used. The system must be compact and robust so the detector can be located within 2 inches of the sample surface.

As defined herein, an online sampling means refers to a sampling means wherein the sample is nonstationary relative to the analyzer. For example, in one embodiment of the present invention, the analyzer remains in a fixed, stationary position adjacent to a moving sample stream. In another embodiment, the sample remains fixed, and the analyzer is scanned across the sample.

By mounting the XRF elemental analyzer in close proximity (<2 inches) to a moving stream of fine coal or ore, it is possible to obtain direct measurements of characteristic Kα and in some cases, K β, X-rays for many of the elements in the Periodic Table between aluminum and silver. In measuring coal composition, X-ray peaks for aluminum, silica, sulfur, chlorine, potassium, calcium, titanium and iron can be obtained. An ash measurement can also be obtained as a function of the major elements in the ash and/or a backscattered ash peak. A microwave transmitter/receiver assembly is used to relate microwave attenuation or phase shift to moisture content.

Computer control of the sample size and frequency synchronized with the X-ray detection system enables each sample increment to be analyzed and combined so that a statistically valid sample can be obtained in accordance with ASTM and/or ISO sampling practice. As with any sampling device, the XRF elemental analyzer analyzes a portion of a sample stream assumed to be (1) homogeneous and (2) representative of the lot.

DETAILED DESCRIPTION OF THE INVENTION

Figure 1:
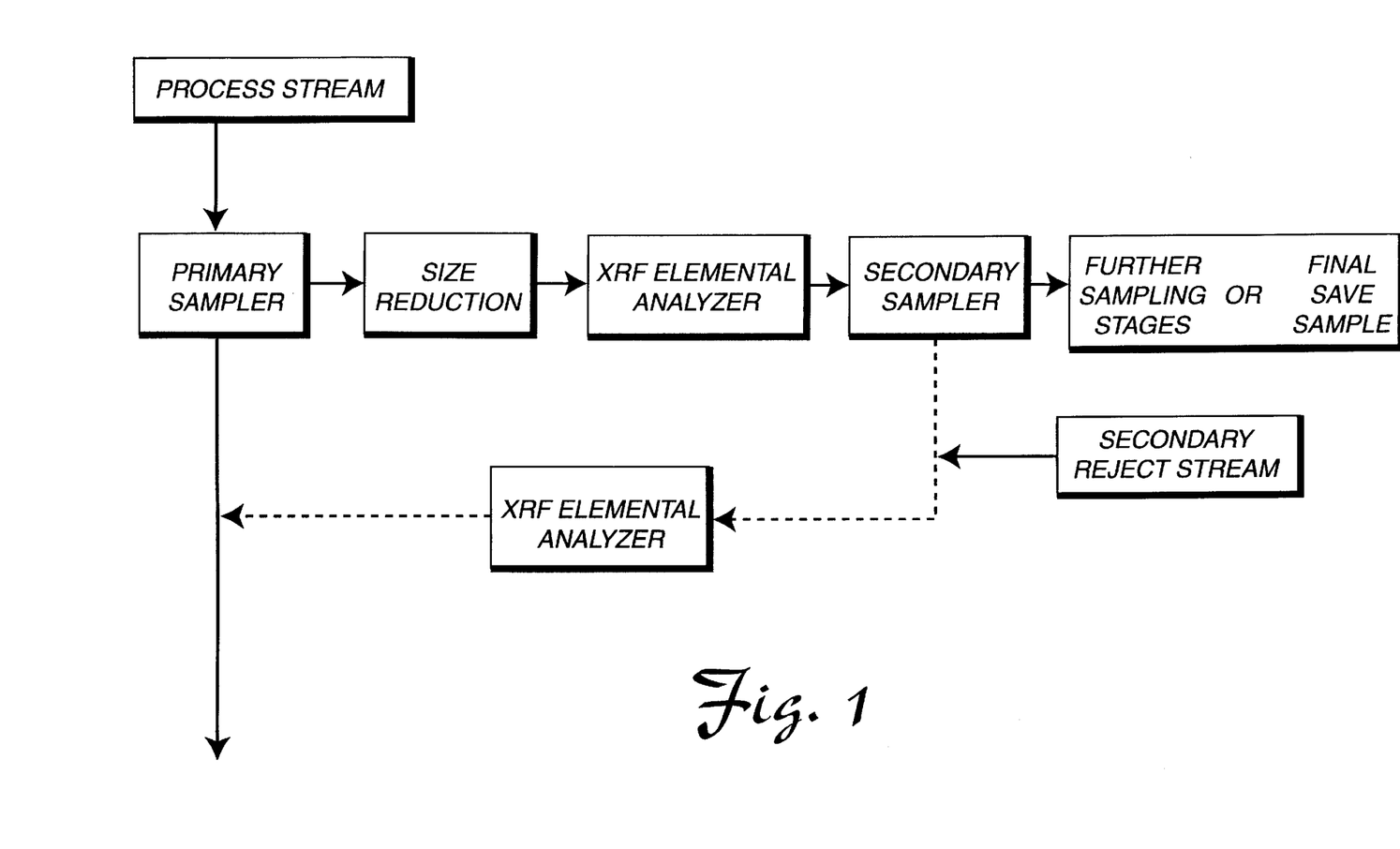
FIG. 1 is a block diagram showing how the XRF Elemental analyzer can be integrated with a mechanical sampling system in a sub-stream configuration.

In a preferred embodiment of the present invention, the XRF elemental analyzer 100 is in a sub-stream configuration as shown in FIG. 1, where part of the process stream to be analyzed is diverted by means of a suitable sampling system for presentation to the on-line analyzer 100. If the coal or ore to be analyzed has a top particle size (95% passing) greater than ⅜ inch or 10 mm, then a size reduction stage is necessary to provide a uniform surface to present to the analyzer 100 for interrogation.

Figure 2:
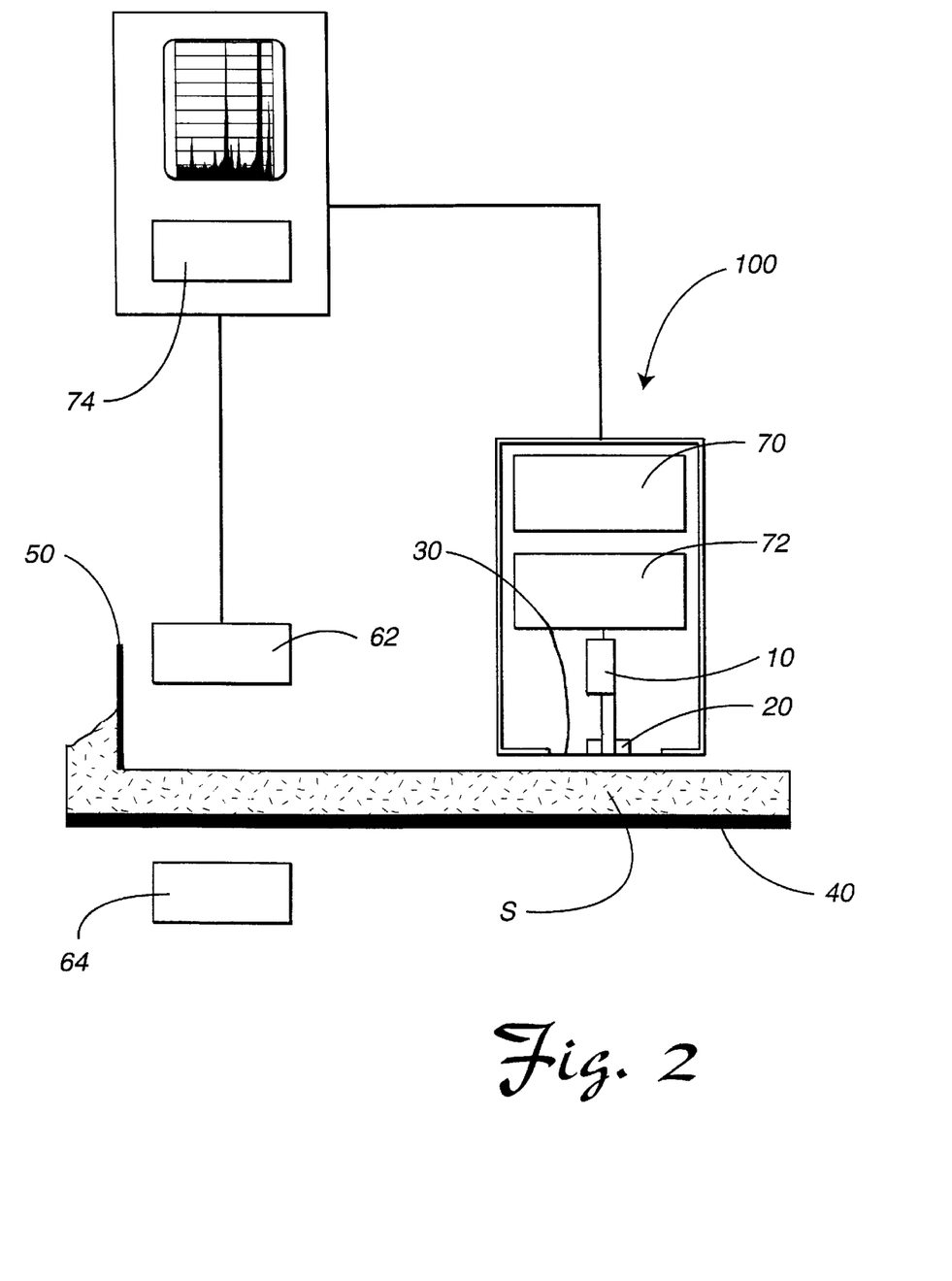
FIG. 2 is a pictorial view of the analyzer mounted on a sampling system with a layer of coal or ore transported through the analyzer interrogation zone. A plow is used to uniformly shape the surface of the sampled material. The physical layout of the major components including the signal processing elements are shown.

FIG. 2 illustrates how the XRF elemental analyzer system 100 is configured when mounted on a mechanical sampling means. A coal or ore sample, typically the primary save (after crushing) or the secondary reject, is conveyed 40 past the analyzer 100. A plow 50 is used to shape the layer or bed of material to be interrogated. If a moisture determination is to be made, a microwave transmitter 64/receiver 62 assembly is mounted above and below the conveyor belt 40 to determine moisture as a function of microwave signal attenuation. The moisture meter also can serve as a sensor to determine the presence of material on the conveyor belt 40. If the microwave signal goes below a threshold limit signaling the presence of material on the conveyor belt 40, the multi-channel analyzer 70 is turned on to acquire counts in as many as 16,000 data channels. In the preferred embodiment, the read-out from the MCA is presented for display by a computer 74 or other type of programmable logic controller, which is also in communication with the microwave receiver 62, if present. An amplifier and power supply 72 also forms a part of the system 100 of the preferred embodiment, and the appropriate signal and power connections 76, 78 are also provided.

Figure 2A:
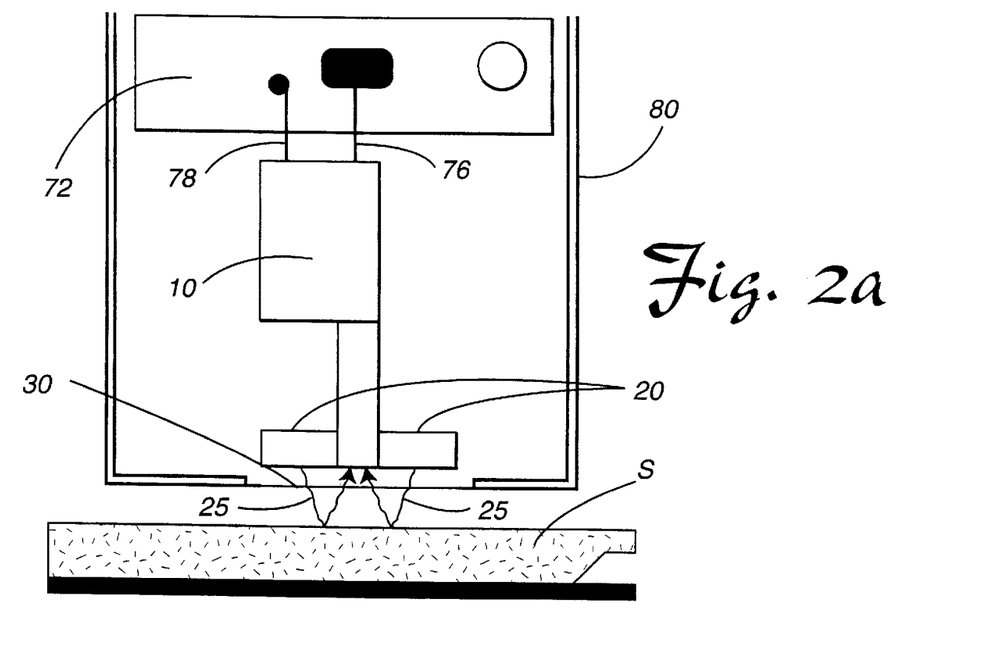
FIG. 2A is an enlarged view of the electronics enclosure and shows a first configuration of the X-ray generators such that the X-ray source transmission axis and the detection axis are parallel to each other and normal (oriented at 90 degrees) to the sample surface.
Figure 2B:
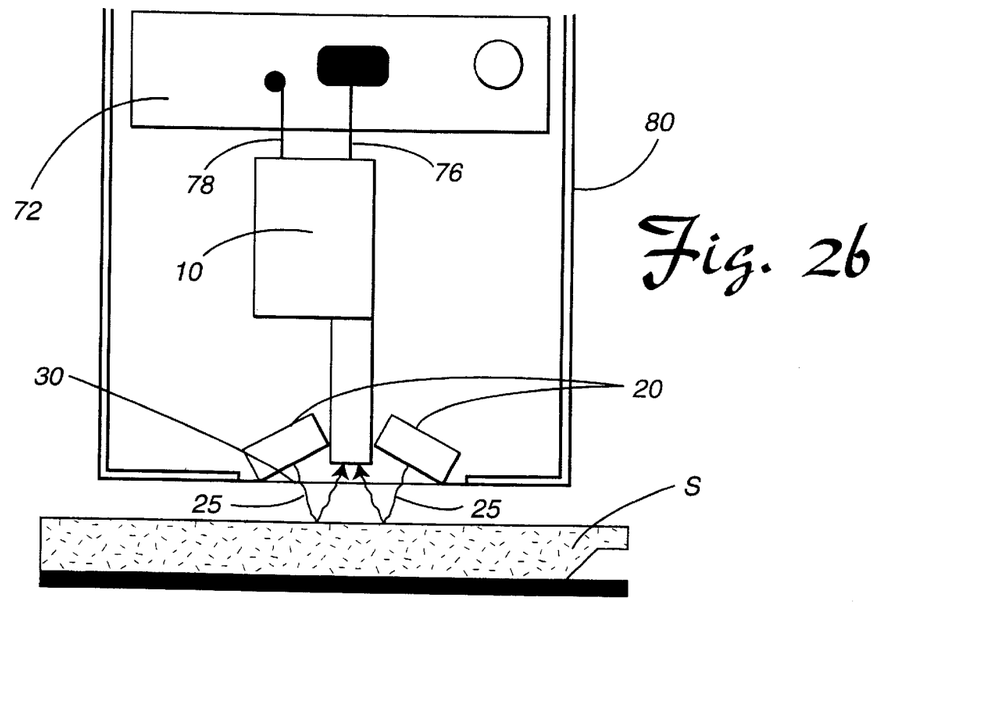
FIG. 2B is an enlarged view of the electronics enclosure and shows a second configuration of the X-ray generators such that the X-ray source transmission axis and the detection axis of the detector are oriented generally perpendicular to the sample surface and are aligned to within 30 degrees of each other.

An X-ray tube or generator 20 is employed to bombard the sample with incident radiation in the 3–20 KeV range (see reference numeral 25 in FIGS. 2a and 2b). Higher energies can be used, but the efficiency of excitation for elements below iron (atomic number 26) in the Periodic Table drops when higher energies are used. An X-ray generator 20 is a pyroelectric crystal that generates energetic electrons which produce X-rays in a target material, i.e., copper or molybdenum. A radioisotope or an X-ray tube can also be used, but is not preferred.

A silicon detector 10 is used to measure the resulting fluorescent radiation (see reference numeral 25 in FIGS. 2a and 2b). The preferred embodiment uses a thermoelectrically cooled Si-PIN photodiode as an X-ray detector. More than one detector 10 may be used if more than one measuring path is necessary to represent the entire sample. Other types of silicon detectors and cooling systems may be applied.

As defined herein, a backscattering geometry is one in which the source 20 and the detector 10 are disposed generally on the same side of the sample. In contrast, a transmission geometry is one in which the source 20 and the detector 10 are on opposite sides of the sample. In the present invention, a backscattering geometry is preferred for the analysis of solid samples. For liquid samples, a transmission geometry may also be used.

The detector(s) 10 and generator(s) 20 are mounted within 2 inches of the surface of the sample. They are protected by a thin window 30 (0.002–0.01 inches) which maintains a sealed environment for the electronics. To minimize attenuation of the low energy X-rays by the window 30, low atomic density materials such as polypropylene or polyethylene is used. The film may be coated with a resin or acrylic to increase durability.

The detector 10 and generator 20 are mounted inside instrument enclosure 80 within a 90 degree angle of each other with as small of an angle between them as possible. As defined herein, the transmission axis of the X-ray source 20 is the axis along which X-ray emission reaches a maximum. The detection axis of the X-ray fluorescence detector 20 is defined as the surface normal of the X-ray fluorescence sensing element of the detector 20. In a preferred embodiment, the X-ray source transmission axis and the detection axis of the detector 20 are oriented generally perpendicular to the sample surface and are aligned to within 30 degrees of each other (FIG. 2B). In a particularly preferred embodiment, the X-ray source transmission axis and the detection axis are parallel to each other and normal (oriented at 90 degrees) to the sample surface (FIG. 2A). In a most preferred embodiment, one or more X-ray generators 20 are placed concentrically around a detector 10 and all of the above are perpendicular to the surface of the sample.

An alternate configuration in which the detector 10 and generator 20 are mounted on the underside of a chute is also possible.

Figure 3:
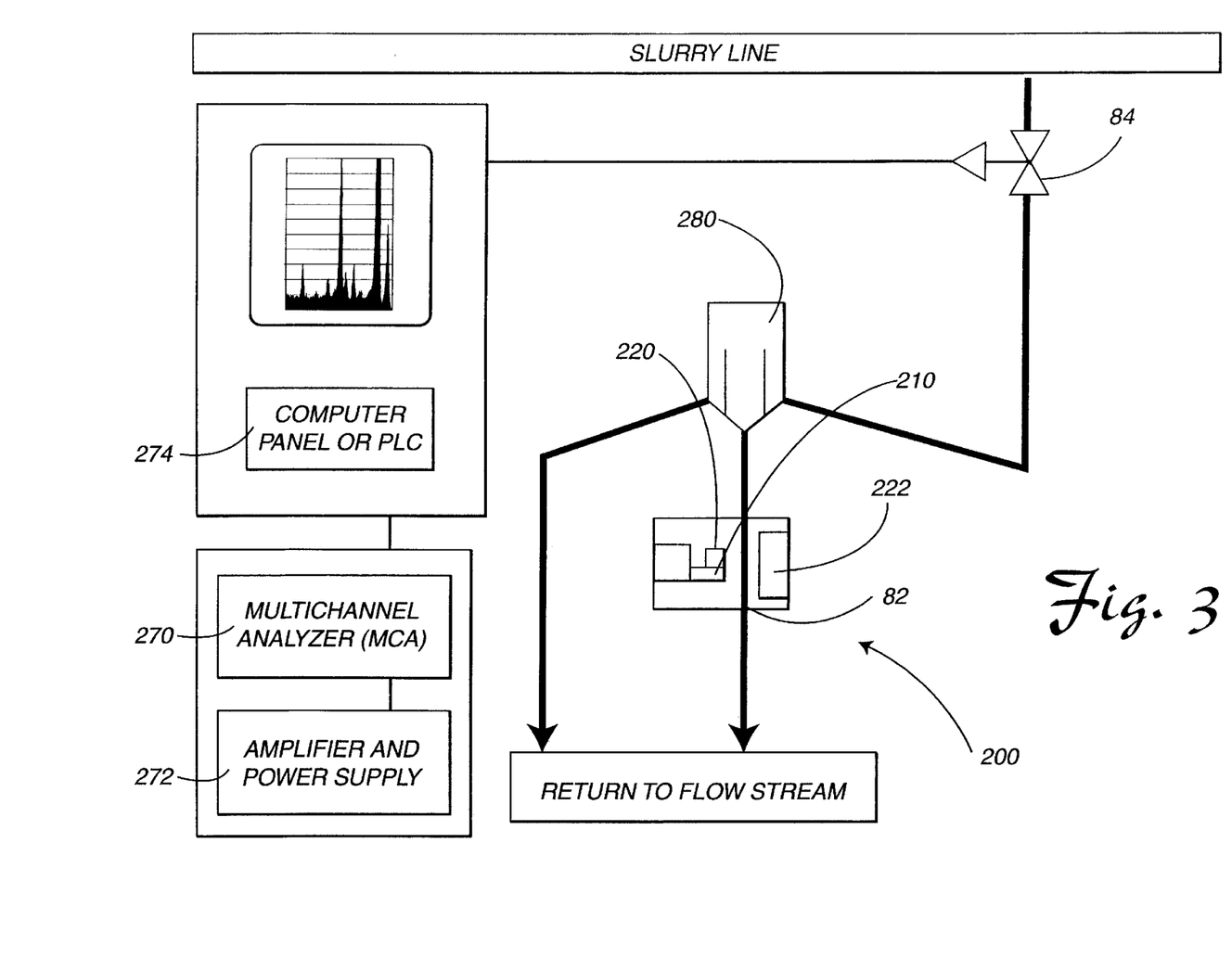
FIG. 3 is a pictorial view of an alternate embodiment where the sample to be analyzed is in slurry form and transported through the interrogation zone in a flow cell. A constant head tank is employed to ensure uniform flow and to minimize air entrainment.

FIG. 3 depicts another embodiment of the XRF elemental analyzer 200 for slurries. In this case, a sample of the flow stream is obtained from a sample cutter inserted into a pipe. A computer actuated valve 84 controls the flow of the slurry sample to the analyzer 200. Samples from around a processing plant can be sequenced to the analyzer 200 in this manner.

A constant head tank 280 ensures a fixed flow rate through the flow cell 82 containing the X-ray detector(s) 210 and generators(s), 222. It also serves as a de-aerator for slurries containing forth or entrained air.

The flow cell 82 holds the detector 210 and generator 220 in the same configuration as described above. Windows are used to seal the electronics in a water tight chamber. This would include a second X-ray source 220 or a separate density gauge used to measure solids concentration by correlating slurry density (% solids) to attenuation of X-rays or $\gamma$-rays. This is done with an incident energy of 20 KeV or higher to minimize the effects of mineralogical composition on the measurement.

In any of the embodiments described, a preamplifier forwards the signal to a shaping amplifier 272 which is connected to the input of a multi-channel analyzer 270 (MCA). The output from the MCA 270 is processed by a computer or programmable logic controller 274 (PLC) to compute the concentrations of various elements in the sample.

Figure 4:
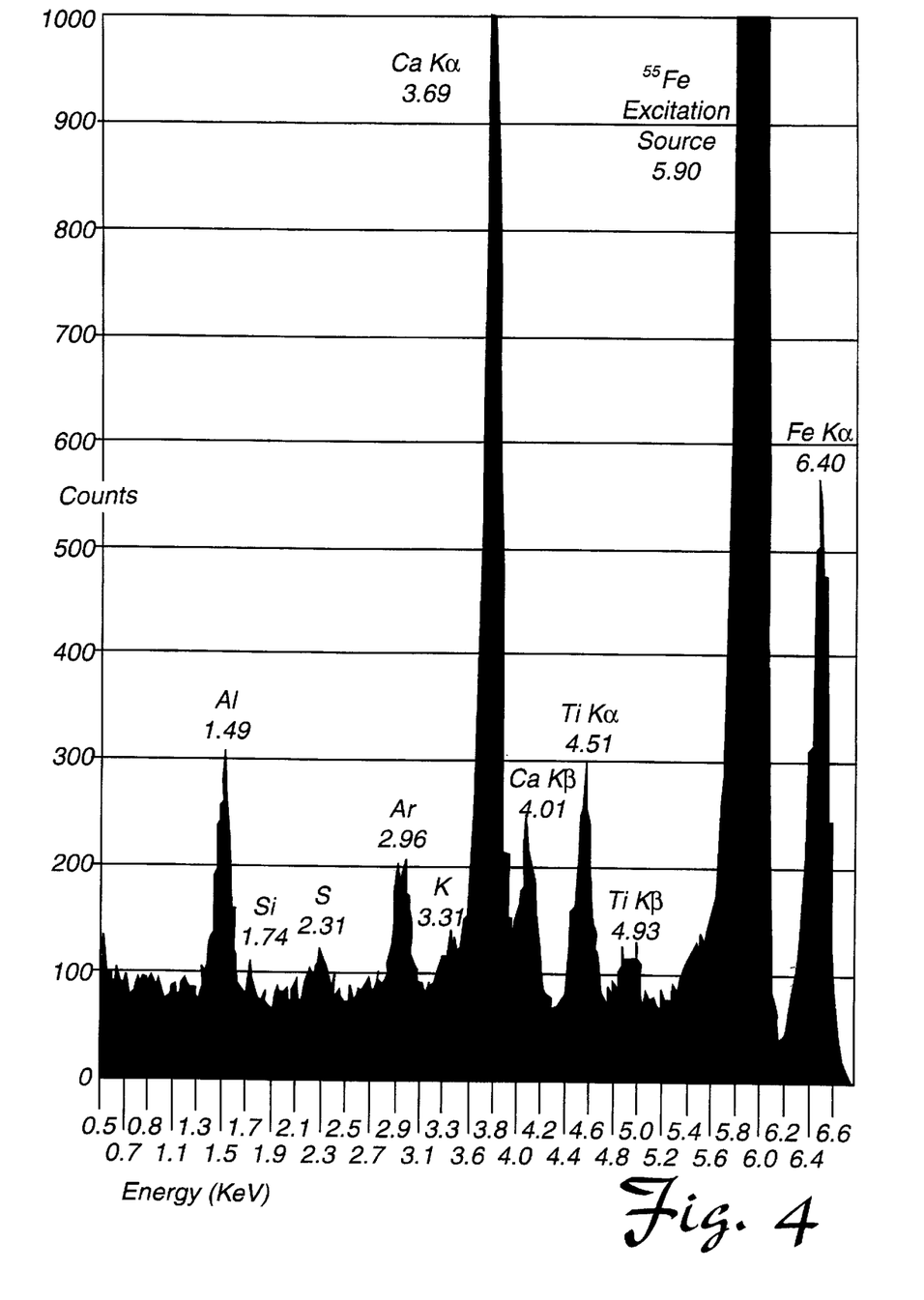
FIG. 4 is a typical X-ray fluorescence spectrum from a sample of coal using a $^{55}$Fe excitation source. An $^{55}$Fe excitation source is equivalent to an X-ray generator with a Cu target.

FIG. 4 provides an example of the output from the MCA 70, 270 representing an elemental analysis of a western U.S. coal. The areas under each peak correlate to the concentration of each element. These are calibrated using a linear, or sometimes a multiple linear regression (if more than one element occurs together in a certain mineralization) with a laboratory elemental analysis of the sample in accordance with ASTM or ISO procedures. Linear calibration equations are possible to low concentrations of even the lightest elements in the range (e.g. sulfur down to concentrations of 0.5% by weight in ash or 0.05% by weight in coal) because the high peak resolution enables the peak to be distinguished from background and proportionality maintained.

In the case of coal analysis, the ash content can be computed as a function of the major elements in the ash and/or a backscattered peak produced by Compton and Raleigh scattering of the incident beam of radiation. The iron content as measured by the fluoresced Fe K$\alpha$ X-rays is used as a term in the equation to correct for fluctuations in iron which disproportionately affects the ash computation.

The apparatus described above directly measures the elemental composition of coal and mineral ores using energy dispersive X-ray fluorescence spectroscopy. It provides an accurate ash measurement by improving upon established methods with the use of iron compensation and can resolve a sulfur peak down to 0.5% weight in ash.

We claim:

1. An apparatus for the online detecting or analyzing of the elements in a sample comprising:
    at least one X-ray source for directing X-rays toward the sample; and
    at least one detector for detecting X-ray fluorescence from the sample and producing signals in response thereto, said X-ray detector being mounted within two inches of the sample to maximize X-ray detection and sensitivity.

2. The apparatus of claim 1, further including an analyzer for determining the elemental composition of said sample based on the signals received from said at least one X-ray fluorescence detector.

3. The apparatus of claim 1 wherein said at least one X-ray source is characterized by a transmission axis and wherein said at least one X-ray fluorescence detector is characterized by a detection axis, and wherein said transmission axis and said detection axis are aligned to within 30 degrees of the sample surface normal.

4. The apparatus of claim 3 wherein said X-ray transmission axis and said detection axis are parallel to each other and normal to the sample surface.

5. The apparatus of claim 1 wherein said at least one X-ray source and said at least one X-ray fluorescence detector are disposed in a backscattering geometry.

6. The apparatus of claim 1, further comprising a thin window disposed between the sample and said at least one X-ray detector.

7. The apparatus of claim 1, wherein said at least one X-ray source produces incident X-rays in the range of 3–20 KeV.

8. The apparatus of claim 1, further including a leveling device to maintain a fixed distance between the sample and said at least one X-ray detector.

9. The apparatus of claim 8, wherein said leveling device comprises a fixed plow or a leveling plate.

10. The apparatus of claim 1 further including a microwave moisture reader.

11. The apparatus of claim 1, further including means for detecting the presence of a sufficient level of material flowing past said at least one X-ray detector to permit repeatable analyses.

12. The apparatus of claim 11 wherein said means for detecting the presence of sufficient sample material comprises a microwave, X-ray or $\gamma$-ray sensor oriented in a transmission geometry.

13. A method for completing online elemental analysis, comprising providing a coal sample;
    directing only X-rays toward the coal sample;
    detecting X-ray fluorescence from the coal sample using an X-ray detector producing signals in response thereto mounted within two inches of the sample; and
    presenting an elemental composition of the coal sample based on the signals produced.

14. The method according to claim 13, further including leveling the coal sample to ensure that the detecting step is repeatable.

15. The method according to claim 13, wherein providing the coal sample includes placing the coal sample on a moving conveyor belt.

16. The method according to claim 13, wherein the directing of only X-rays is completed by at least one X-ray source.

17. The method according to claim 16, wherein said at least one X-ray source is characterized by a transmission axis, said at least one X-ray fluorescence detector is characterized by a detection axis, and wherein X-ray transmission axis and said detection axis are parallel to each other and normal to the coal sample.

18. An apparatus for online elemental analysis of a sample comprising:
    at least one X-ray source for directing X-rays toward the sample;
    at least one X-ray fluorescence detector for detecting X-ray fluorescence from the sample and for producing signals in response thereto, said at least one X-ray fluorescence detector being disposed in a backscattering geometry; and an analyzer for determining the elemental composition of said sample based on the signals received from said at least on X-ray fluorescence detector;

said at least one X-ray source being characterized by a transmission axis and said at least one X-ray fluorescence detector being characterized by a detection axis, said X-ray transmission axis and said detection axis being parallel to each other and normal to the sample surface.

19. An apparatus for the online detecting or analyzing of the elements in a sample comprising:

at least two X-ray sources for directing X-rays toward the sample; and at least one X-ray fluorescence detector for detecting X-ray fluorescence form the sample and for producing signals in response to said X-ray fluorescence, wherein said X-ray fluorescence detector is mounted between said at least two X-ray sources in a backscattering geometry.

20. The apparatus according to claim 19, wherein said at least two X-ray sources are each characterized by a transmission axis, said at least one X-ray fluorescence detector is characterized by a detection axis, and each said transmission axis and said detection axis are aligned to within 30 degrees of the sample surface normal.

21. The apparatus according to claim 19, wherein each of said at least two X-ray sources is characterized by a transmission axis, said at least one X-ray fluorescence detector is characterized by a detection axis, and said each transmission axis and said detection axis are parallel to each other and normal to the sample surface.

22. The apparatus according to claim 19, further including an analyzer for determining the elemental composition of said sample based on the signals received from said at least one X-ray fluorescence detector.

* * * * *

(12) EX PARTE REEXAMINATION CERTIFICATE (9238th)
United States Patent
Laurila et al.

(10) Number: US 6,130,931 C1
(45) Certificate Issued: Aug. 28, 2012

(54) X-RAY FLUORESCENCE ELEMENTAL ANALYZER

(75) Inventors: Melvin J. Laurila, Lake Zurich, IL (US); Claus C Bachmann, Bad Wilbad (DE); Albert P. Klein, Simmersfeld (DE)

(73) Assignee: Elisabeth Katz, Simmersfeld (DE)

Reexamination Request:
No. 90/010,580, Jul. 10, 2009

Reexamination Certificate for:
Patent No.: 6,130,931
Issued: Oct. 10, 2000
Appl. No.: 09/156,078
Filed: Sep. 17, 1998

(51) Int. Cl.
*G01V 5/00* (2006.01)
*G01N 23/223* (2006.01)
*G01N 23/22* (2006.01)
*G01N 23/04* (2006.01)
*G01N 23/00* (2006.01)

(52) U.S. Cl. ............................. 378/45; 378/44; 378/54; 378/55

(58) Field of Classification Search .................. 378/45
See application file for complete search history.

(56) References Cited

To view the complete listing of prior art documents cited during the proceeding for Reexamination Control Number 90/010,580, please refer to the USPTO's public Patent Application Information Retrieval (PAIR) system under the Display References tab.

*Primary Examiner* — Christopher E Lee (57) ABSTRACT

An apparatus for measuring the composition of coal and mineral ores on-line, by bombarding a sample stream with low energy X-rays and measuring the characteristic X-rays fluoresced. The assembly is comprised of one or more X-ray generators mounted in a specific geometry with one or more silicon detectors. A representative sample of a flow stream is obtained from a sampling system. Sample presentation to the analyzer is done with a plow or a flow cell to obtain a uniform interrogation zone for the analyzer. Elemental analysis (Aluminum through Silver on the Periodic Table) of the sample is computed from calibration curves generated from a linear relationship with count rates under each peak. Sample presentation to the analyzer is done with a plow or leveling plate to ensure that material flows past the analyzer at a constant level. The elemental analysis is determined by measuring counts under the characteristic peaks fluoresced by various elements in an energy spectrum resolved with a multi-channel analyzer.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 2 and 5-12 is confirmed.

Claims 1, 3 and 4 are cancelled.

Claims 13-15, 17 and 18 are determined to be patentable as amended.

Claim 16, dependent on an amended claim, is determined to be patentable.

New claims 23 and 24 are added and determined to be patentable.

Claims 19-22 were not reexamined.

13. A method for completing online elemental analysis, comprising providing a coal sample *within a process stream*;

directing only X-ray toward the coal sample *within the process stream*;

detecting X-ray fluorescence from the coal sample *within the process stream* using an X-ray detector producing signal in response thereto mounted within two inches of the sample *within the process stream*; and presenting an elemental composition of the coal sample *within the process stream* based on the signals produced.

14. The method according to claim 13, further including leveling the coal sample *within the process stream* to ensure that the detecting step is repeatable.

15. The method according to claim 13, wherein providing the coal sample *within the process stream* includes placing the coal sample on a moving conveyor belt.

17. The method according to claim 16, wherein said at least one X-ray source is characterized by a transmission axis, said at least one X-ray fluorescence detector is characterized by a detection axis, and wherein X-ray transmission axis and said detection axis are parallel to each other and normal to the coal sample *within the process stream*.

18. An apparatus for online elemental analysis of a sample *from a process stream* comprising:

at least one X-ray source for directing X-ray toward the sample *from the process stream*;

at least one X-ray fluorescence detector for detecting X-ray fluorescence from the sample *from the process stream* and for producing signals in response thereto, said at least one X-ray fluorescence detector being disposed in a backscattering geometry; and an analyzer for determining the elemental composition of said sample *from the process stream* based on the signals received from said at least on X-ray fluorescence detector;

said at least one X-ray source being characterized by a transmission axis and said at least one X-ray fluorescence detector being characterized by a detection axis, said X-ray transmission axis and said detection axis being parallel to each other and normal to the a sample surface.

*23. An apparatus for the online detecting or analyzing of the elements in a sample comprising;*

*at least one X-ray source for directing X-rays toward the sample;*

*at least one detector for detecting X-ray fluorescence from the sample and producing signals in response thereto, said X-ray detector being within two inches of the sample to maximize X-ray detection and sensitivity, wherein said at least one X-ray source and said at least one detector for detecting X-ray fluorescence are disposed in a backscattering geometry;*

*an analyzer for determining the elemental composition of said sample based on the signals received from said at least one X-ray fluorescence detector;*

*a thin window disposed between the sample and said at least one X-ray detector;*

*a leveling device to maintain a fixed distance between the sample and said at least one X-ray detector; wherein said leveling device comprises a fixed plow or a leveling plate.*

*24. An apparatus for the online detecting or analyzing of the elements in a sample within a moving process stream comprising:*

*at least X-ray source for detecting X-rays toward the sample within the moving process stream; and*

*at least one detector for detecting X-ray fluorescence from the sample within the moving process stream and producing signals in response thereto, said X-ray detector being mounted more than one-half inch from the sample within the moving process stream but within two inches of the sample within the moving process stream to maximize X-ray detection and sensitivity.*

* * * * *